United States Patent
Saveliev et al.

(10) Patent No.: US 8,139,222 B2
(45) Date of Patent: Mar. 20, 2012

(54) PRESSURE CONTROLLED SPECTROSCOPIC HEATING VALUE SENSOR

(75) Inventors: Alexei Saveliev, Cary, NC (US); Serguei Zelepouga, Hoffman Estates, IL (US); David M. Rue, Chicago, IL (US)

(73) Assignee: Gas Technology Institute, Des Plaines, IL (US)

( * ) Notice: Subject to any disclaimer, the term of this patent is extended or adjusted under 35 U.S.C. 154(b) by 281 days.

(21) Appl. No.: 12/715,006

(22) Filed: Mar. 1, 2010

(65) Prior Publication Data

US 2011/0211193 A1  Sep. 1, 2011

(51) Int. Cl.
*G01N 21/31* (2006.01)
(52) U.S. Cl. .................. 356/432; 356/436; 356/306
(58) Field of Classification Search .......... 356/432–440, 356/306, 300

See application file for complete search history.

(56) References Cited

U.S. PATENT DOCUMENTS 7,248,357 B2   7/2007  Servaites et al.
2010/0028980 A1*  2/2010  Hasson et al. ............. 435/286.5

* cited by examiner

*Primary Examiner* — Hoa Pham
(74) *Attorney, Agent, or Firm* — Mark E. Fejer

(57) ABSTRACT

A method and system for measuring a physical property of a fluid in which light having wavelengths in the near-infrared is directed into a test cell containing the fluid and portions of the light not absorbed by the fluid and passing out of the cell are spatially dispersed by wavelength, forming a light spectrum that is projected onto a detector. The light spectrum is digitized and inputted into a data processing unit in which it is compared to the actual spectrum of the light source stored in the system to determine the absorbance spectrum of the fluid. The system is spectrally calibrated by identifying known spectral features of the fluid absorbance spectrum. To correct for deviations in the original light source spectrum, a calibration method in which the pressure of the fluid in the test cell is alternated between a first positive pressure and a second positive pressure is employed. Upon determination of the absorbance spectrum of the fluid, the physical property of interest of the fluid is determined by comparing the absorbance spectrum to a plurality of spectra located within an on-board database.

19 Claims, 4 Drawing Sheets

PRESSURE CONTROLLED SPECTROSCOPIC HEATING VALUE SENSOR

BACKGROUND OF THE INVENTION

1. Field of the Invention

This invention relates to a method and apparatus for the measurement of a physical property of a fluid that is dependent upon a physical characteristic of at least one functional group and that is related to the quantity of that functional group in the fluid. In one aspect, this invention relates to the measurement of the heating value of a fuel gas at-line and in real-time. In one aspect, this invention relates to a method of self-calibration for an apparatus for measuring the physical property of interest of a fluid, such as the heating value of a combustible gaseous fuel mixture. In one aspect, this invention relates to a method and apparatus for measuring the heating value of a combustible gaseous fuel mixture, including functional groups and molecules, using near-infrared absorption spectroscopy.

2. Description of Related Art

Historically, the heat energy content of a combustible fluid was determined by burning precisely defined amounts of the fluid, such as natural gas, to determine the amount of energy produced from the combustion. Other methods determined concentration of each whole combustible compound in the mixture, defining the energy content for each whole combustible compound, and summing them to yield the heat energy content of the entire mixture.

The heat energy content of natural gas flowing through a pipeline, which natural gas typically contains methane, ethane, propane, and higher alkane hydrocarbons, frequently fluctuates, even over relatively short periods of time. Conventional methods of measurement generally require bypass flow-lines or fluid extraction to provide gas samples which are then taken to a lab and burned. The temperature of the flame is then measured. Available sensors for making these measurements are primarily comprised of calorimeters and gas chromatographs. Disadvantageously, such devices, in addition to requiring the removal of samples from pipelines, have slow response times, and have high initial and maintenance costs. It is difficult to both continuously and accurately measure the energy content of natural gas in pipelines, and the lack of any convenient means for making such continuous and accurate measurements may result in improper charges during the course of a day to the disadvantage of both buyers and sellers.

One method and apparatus for addressing the need for both continuous and accurate measurement of the heat energy content of combustible gaseous fluid mixtures is described in U.S. Pat. No. 7,248,357, which is incorporated herein in its entirety by reference. As described therein, a method and system is provided for measuring the heat energy of a combustible fluid in which radiation means direct radiation through a sample of the combustible fluid, detection means detect absorbance of at least one combustible components of the combustible fluid at a selected spectral line, where there is at least one spectral line for each combustible component to be considered in the combustible fluid, calibration means calibrate the source of the radiation, storage means store a plurality of spectra of combustible gas mixtures, thereby enabling comparison of the measured absorbance spectrum to the plurality of spectra, combination means combine at least one heat energy proportional factor with the absorbance at each spectral line, and summing means sum the combinations to determine the heat energy of the combustible fluid. The system continuously acquires absorption spectra from gases in the near-infrared region. The near-infrared region of the electromagnetic spectrum is particularly useful because combustible gas components, in particular methane, ethane, propane, butane, iso-butane, and hexane produce strong absorbent spectra in this spectral range. The measurement of absorption values at several predetermined wavelengths allows reconstruction of fuel composition and heating value using specially developed mathematical algorithms. The absorbance value is calculated as $$A = \ln\left[\frac{I_0}{I}\right]$$

where $I_0$ is the light intensity measured with an optical cell filled by purging gas and I is the intensity of light measured with the cell filled with a fuel. Calibration (zeroing) of the system requires periodic flushing of the optical cell with a purging gas, such as nitrogen or air. The disadvantages of this calibration method include system complexity due to the requirements for a purging gas supply and additional valves and controls and interruption in sensor monitoring when purging is taking place.

FIG. 1 is a schematic diagram of a conventional spectroscopic heating value sensor. As shown therein, the sensor comprises optical cell 10 having optical windows 11, 12 and input and output gas connectors 13 and 14. Periodic switching between fuel and purging gas flows is performed by valve 20. A stabilized light source 21 produces a light beam 22 that is passed through the cavity 23 of the optical cell. The light exiting the optical cell through optical window 12 is dispersed by spectroscopic instrument 24 and directed to a near-infrared sensor array 25 measuring absorption at various wavelengths. The resulting signal is amplified by amplifier 26 and provided to data processor 27 for processing.

FIG. 2 shows the characteristic variations of pressure, P, fuel concentration, F, and light absorption, I, at a given wavelength with time for a gaseous fuel sample. As shown therein, the pressure is constant during the process. The fuel/purging gas flow is altered with valve 20, resulting in a periodic change of fuel concentration with time. The variation in fuel concentration results in changes of absorption signal I from its maximum value $I_0$ corresponding to purged cell conditions to the level obtained with the optical cell completely filled by fuel, $I_F$. The absorption value is calculated as $$A = \ln\left(\frac{I_0}{I_F}\right)$$

The characteristic time of the cycle $t_c$ is limited by the requirement of flushing the cell completely and is typically about five minutes, during a substantial portion of which sensor monitoring of the sample gas cannot be conducted.

SUMMARY OF THE INVENTION

Accordingly, it is one object of this invention to provide a method and apparatus for measuring a physical property of a fluid, such as a composition that is dependent upon a physical characteristic of at least one functional group and is related to the quantity of that functional group in the fluid in which the time cycle, $t_c$, is substantially reduced compared with conventional methods and apparatuses.

It is another object of this invention to provide a method and apparatus for measuring a physical property of the fluid using optical means including an optical cell for containment of a sample fluid which does not require purging of the optical cell for calibration.

These and other objects of this invention are addressed by a method and apparatus in which a sample fluid is introduced into an optical cell having a fluid inlet and a fluid outlet and radiation means for directing radiation through said optical cell, in optical communication with the optical cell, for example, by way of an optical fiber bundle, is passed through the optical cell for detection by a suitable detection means. As the radiation is passing through the optical cell, the pressure of the sample fluid in the optical cell is alternated between a first positive pressure and a second positive pressure and the intensity of the radiation after passing through the optical cell is measured at the first positive pressure and the second positive pressure. Thereafter, a base intensity of the radiation passing through the optical cell is determined, where the base intensity corresponds to the zeroing intensity measured in conventional methods when the optical cell is filled with a purge gas. The absorbance spectrum of the sample fluid is determined and compared with a plurality of spectra located within the database from which comparison at least one physical property of the sample fluid is determined. The absorbance spectrum is determined by spatially dispersing the radiation after passing through the optical cell, thereby forming a radiation spectrum. The radiation spectrum is projected onto a detector and compared with an actual spectrum of the radiation source. In accordance with one embodiment of this invention, the radiation means comprises at least one stabilized light source and a light dispersing element disposed between the optical cell and the detection means. The stabilized light source provides light having wavelengths in the near-infrared and is preferably selected from a group consisting of an incandescent lamp, at least one light emitting diode, and combinations thereof.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

The method and apparatus of this invention for determining a physical property of a fluid utilizes controlled pressure variation to generate independent reference points for absorption measurement. It is to be understood that, although the method and apparatus of this invention are described herein as being applied to a fuel gas or combustible fluid, the method and apparatus may be applied to any gaseous fluid having a physical property that is dependent upon a physical characteristic of at least one functional group and that is related to the quantity of that functional group in the fluid.

Figure 1:
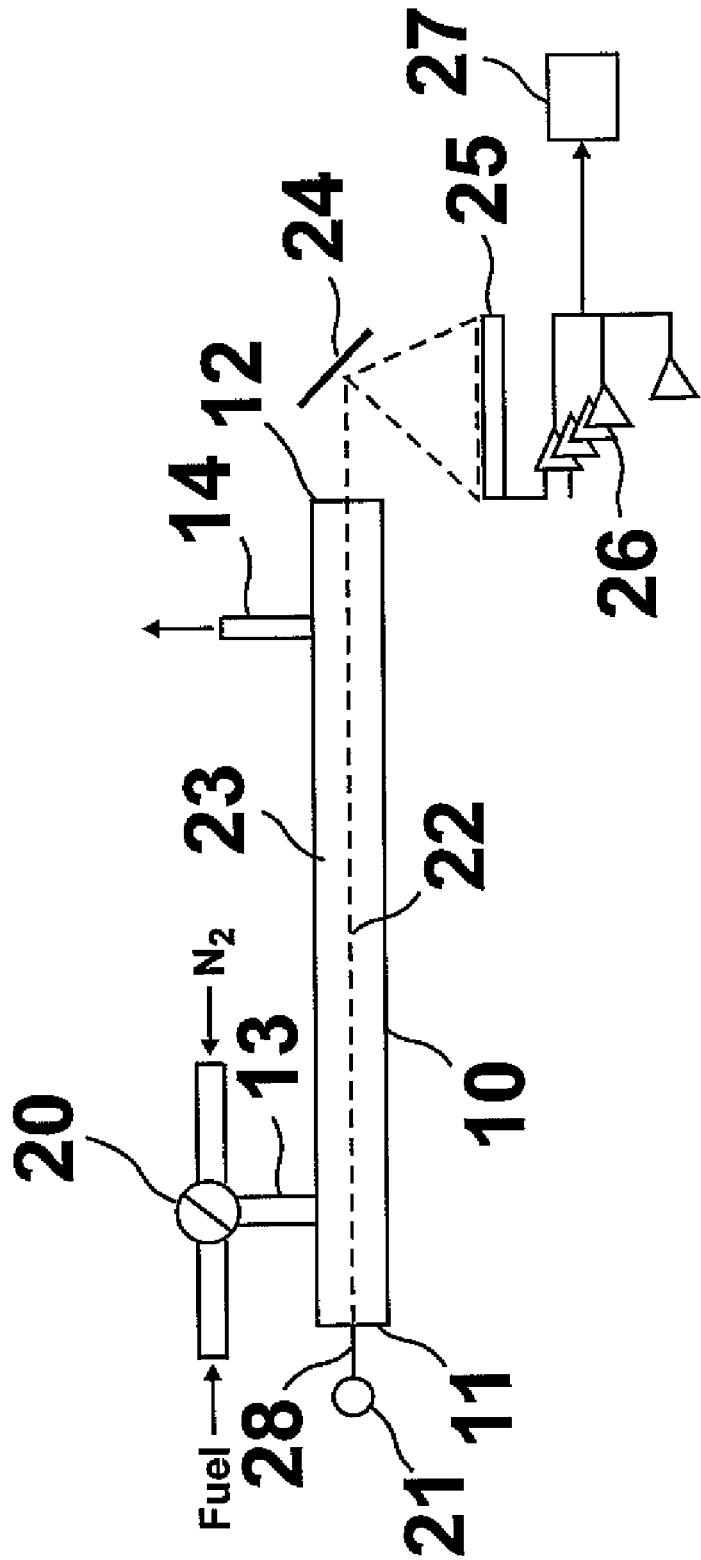
FIG. 1 is a schematic diagram of a conventional spectroscopic sensor for measuring a physical property of a fluid.
Figure 2:
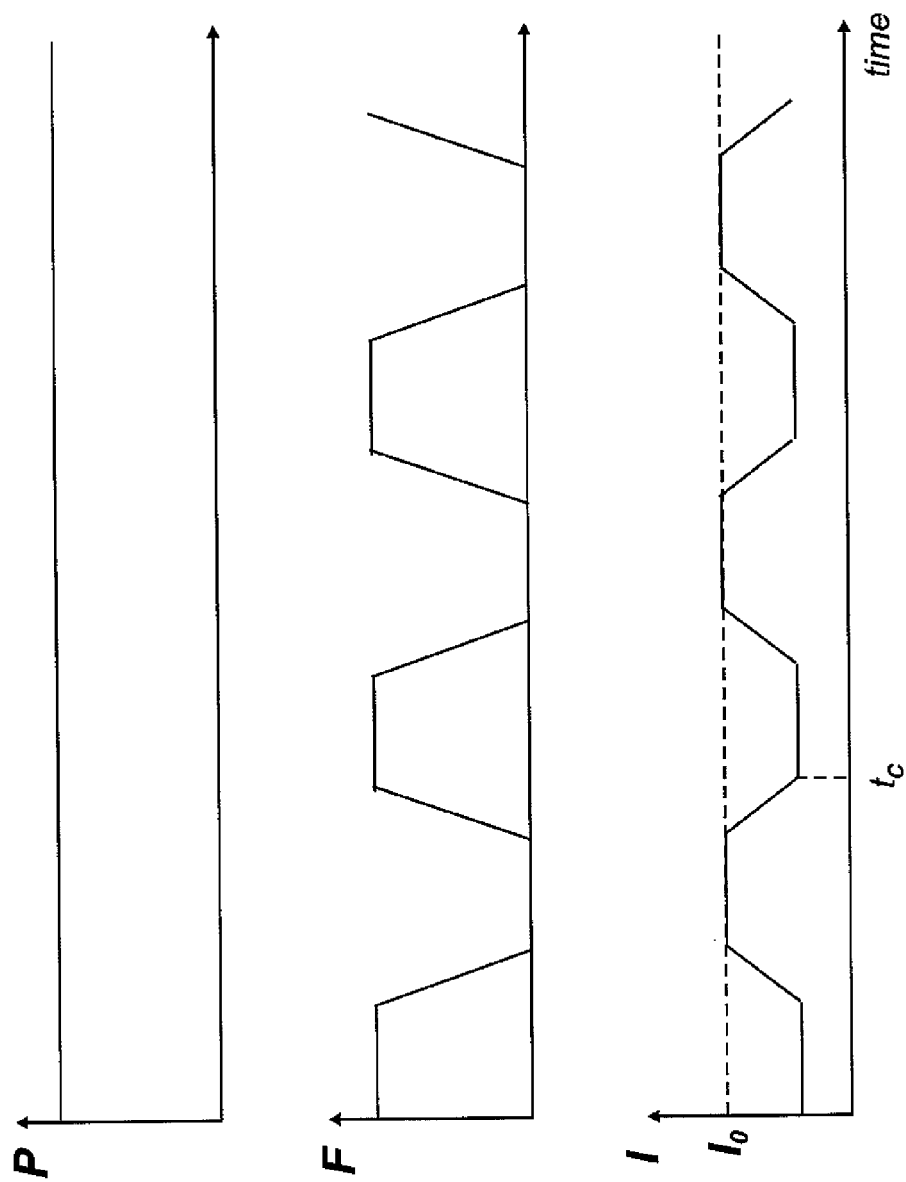
FIG. 2 is a diagram showing the characteristic variations in pressure, fuel concentration and light absorption at a given wavelength with time using a conventional spectroscopic heating value sensor.
Figure 3:
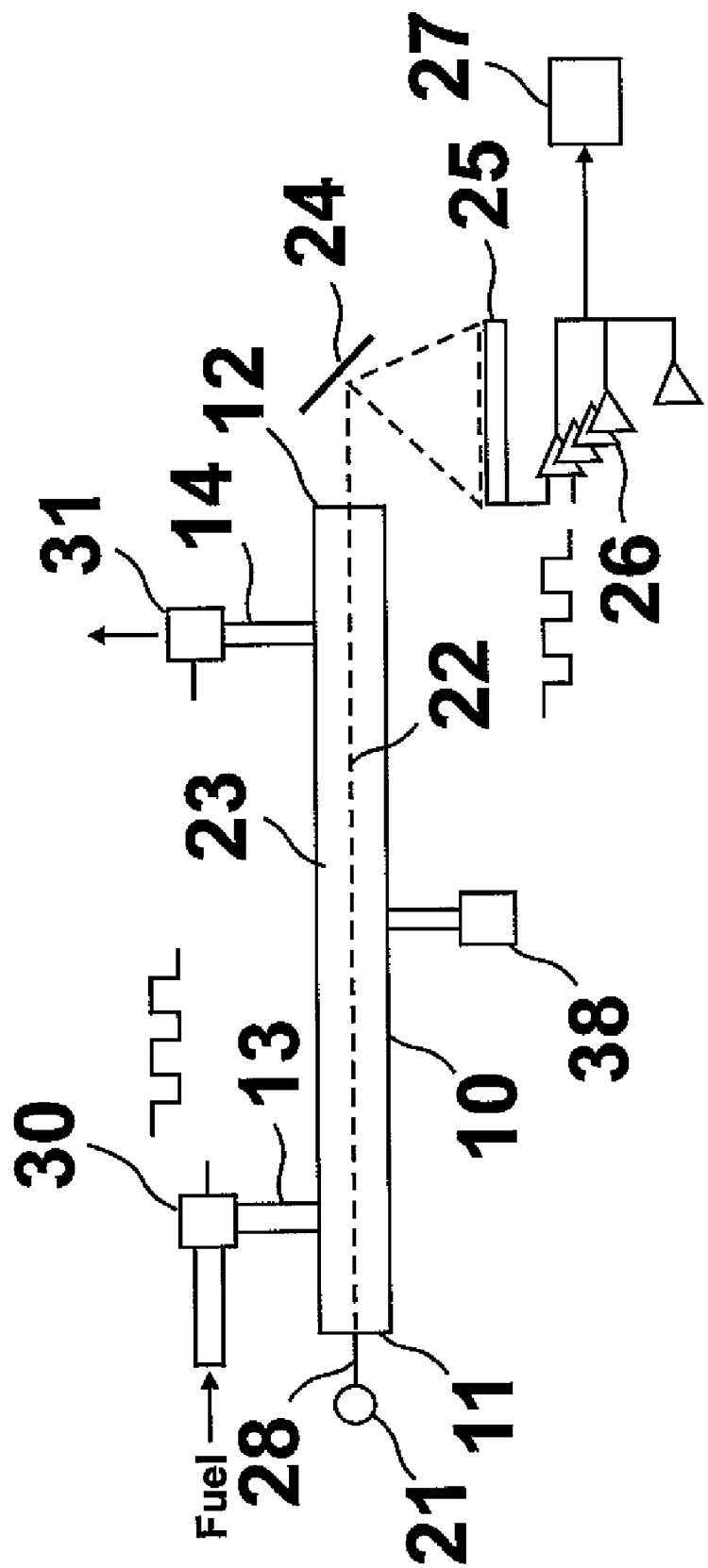
FIG. 3 is a schematic diagram of a spectroscopic sensor in accordance with one embodiment of this invention.

A schematic diagram of a spectroscopic heating value sensor in accordance with one embodiment of this invention for use in the method of this invention is shown in FIG. 3. As shown therein, the sensor comprises optical cell 10 having optical windows 11, 12 and input and output gas connectors 13 and 14, a stabilized light source 21 in optical communication with the optical cell, for example, by way of optical fiber bundle 28, producing a light beam 22 that is passed through the cavity 23 of the optical cell, a spectroscopic instrument 24 for dispersion of the light exiting the optical cell, and a near-infrared sensor array for receiving the dispersed light and measuring absorption at various wavelengths. The stabilized light source is selected from a group consisting of an incandescent lamp, at least one light emitting diode, and combinations thereof. The sensor further comprises pressure control means for periodically changing fluid pressure in the optical cell from a first positive pressure to a second positive pressure. In accordance with one embodiment of this invention, the pressure control means comprises an inlet pressure regulator 30 in fluid communication with input gas connector 13 through which a sample fluid is introduced into the optical cell and an outlet pressure regulator 31 in fluid communication with output gas connector 14 through which the sample fluid is withdrawn from the optical cell. A pressure transducer 38 is provided for measuring the pressure of the sample fluid in the optical cell. The pressure on the sample fluid flowing through the optical cell is controlled by the pressure regulators.

Figure 4:
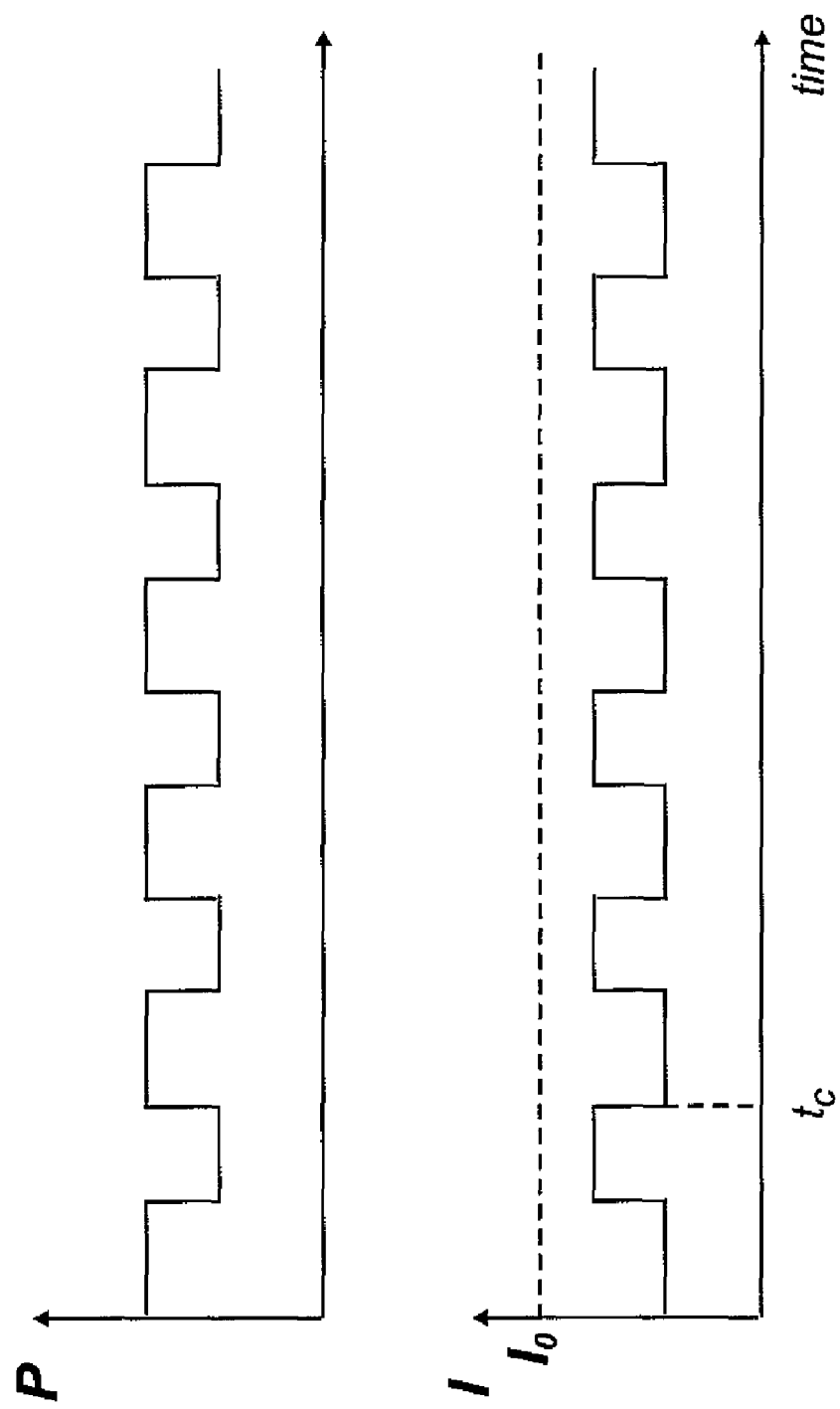
FIG. 4 is a diagram showing the characteristic variations in pressure, fuel concentration and light absorption at a given wavelength with time using a spectroscopic heating value sensor in accordance with one embodiment of this invention.

During operation of the spectroscopic heating value sensor of this invention, the pressure in the optical cell alternates periodically at a frequency in the range of about 1 to about 10 Hz between the first positive pressure and the second positive pressure. A characteristic time of a fuel gas composition variation typically exceeds 1 minute. In this case, the concentration can be considered constant during the pressure variation and the pressure variation can be used for self-calibration purposes. The resulting variation of pressure and absorption signal is shown in FIG. 4. As can be seen, the absorption by the sample fluid increases as the pressure in the optical cell drops closely following the pressure variation profile. Considering that pressure and concentration are related by the natural gas law $$P_1 = n_1 kT$$

$$P_2 = n_2 kT$$

one can derive using the Beer-Lambert law $$I_1 = I_0 \exp\left(-K_F L \frac{P_1}{kT}\right)$$

$$I_2 = I_0 \exp\left(-K_F L \frac{P_2}{kT}\right)$$

where $K_F$ is the absorption constant for the sample fluid at a given wavelength, L is the optical length of the optical cell, T is the temperature of the optical cell, and k is the Boltzmann constant. From here $$\frac{I_1}{I_2} = \exp\left(K_F L \frac{P_2 - P_1}{KT}\right)$$

$$\ln\left(\frac{I_1}{I_2}\right) = K_F L \frac{\Delta P}{kT}$$

$$I_0 = I_2 \left(\frac{I_1}{I_2}\right)^{\frac{P_2}{\Delta P}}$$

and the absorbance is found as $$A = \frac{P_1}{\Delta P} \ln\left(\frac{I_1}{I_2}\right)$$

A similar procedure may be applied to find the absorbance values at several discrete wavelengths that can be further converted to mixture component concentrations using a calibration matrix. In the case of periodic pressure modulation, the high frequency variation of the light intensity may be utilized for signal amplification using a lock-in amplifier 26 that allows extraction of a signal with a predetermined carrier waveform. Other pressure calibration waveforms, e.g. single self-calibrating pressure pulses, may be utilized depending on the specific instrument configuration.

To provide the highest accuracy, care must be taken in the instrument operation. First, the temperature must be monitored along with the pressure because temperature is a variable in the governing equations, and inaccuracy in the temperature affects the accuracy of the results. Gas temperature will not cycle as fast as the 1 to 10 Hz pressure changes, but compensation for temperature variations using temperature changes measured by ultra-high fast thermocouples or calculated by the gas laws will improve accuracy. Second, the range of pressure change must be large enough to provide accurate data on changes in light intensity but not so large as to be difficult to achieve or to cause instabilities in operation or temperature. Pressure changes of about 1% to about 75% of the total pressure may be employed, with preferred changes being in the range of about 5% to about 25%. Third, the pressure changes must be generated in such a way that when readings are taken, the optical cell is at the desired, steady pressure, either the first positive pressure or the second positive pressure. A square wave pressure variation as shown in FIG. 4 is ideal, but any pattern may be used as long as the cell pressure is unchanged long enough to be stable and a known value at both the first positive pressure and the second positive pressure is selected.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An apparatus for measuring a physical property of a fluid comprising:
    an optical cell having a fluid inlet and a fluid outlet;
    radiation means for directing radiation through said optical cell in optical communication with said optical cell;
    detection means for detecting absorbance of said fluid in said optical cell;
    pressure control means for periodically alternating fluid pressure in said optical cell between a first positive pressure and a second positive pressure; and
    a data processor comprising storage means for storing a plurality of absorbance spectra of known fluids, comparison means for comparing said absorbance with said plurality of absorbance spectra, and analyzing means for determining a physical property of said fluid using an output of said comparison means.

2. The apparatus of claim 1, wherein said radiation means comprises at least one stabilized light source.

3. The apparatus of claim 2, wherein said at least one stabilized light source is selected from a group consisting of an incandescent lamp, at least one light emitting diode, and combinations thereof.

4. The apparatus of claim 2, wherein said optical communication comprises at least one optical fiber bundle extending between said stabilized light source and said optical cell.

5. The apparatus of claim 1, wherein said pressure control means comprises a pressure transducer operably connected with said optical cell for measuring said fluid pressure.

6. The apparatus of claim 5, wherein said pressure control means comprises a pressure regulator operably connected with said optical cell for alternating said fluid pressure.

7. The apparatus of claim 1, wherein said radiation means comprises a light dispersing element disposed between said optical cell and said detection means, said light dispersing element adapted to disperse light transmitted from said optical cell to said detection means.

8. An apparatus for measuring a physical property of a fluid comprising:
    at least one light transmissive wall enclosing an optical cell cavity and forming a cavity fluid inlet and a cavity fluid outlet;
    a stabilized light source adapted to transmit light through said optical cell cavity in optical communication with said optical cell cavity;
    light detection means for detecting absorbance of said fluid when said fluid is disposed in said optical cell cavity;
    pressure control means for periodically alternating fluid pressure in said optical cell cavity between to first positive pressure and a second positive pressure; and
    a data processor comprising storage means for storing a plurality of absorption spectra of known fluids, comparison means for comparing said absorbance with said plurality of absorption spectra, and analyzing means for determining a physical property of said fluid using an output of said comparison means.

9. The apparatus of claim 8, wherein said stabilized light source is selected from the group consisting of an incandescent lamp, at least one light emitting diode, and combinations thereof.

10. The apparatus of claim 8, wherein said pressure control means comprises a pressure transducer optically connected with said optical cell for measuring said fluid pressure.

11. The apparatus of claim 10, wherein said pressure control means comprises a pressure regulator operably connected with one of said cavity fluid inlet and said cavity fluid outlet.

12. The apparatus of claim 8 further comprising a light dispersing element disposed between said optical cell cavity and said light detection means, said light dispersing element adapted to disperse light transmitted from said optical cell cavity to said light detection means.

13. The apparatus of claim 8, wherein said optical communication comprises at least one optical fiber bundle extending between said stabilized light source and said optical cell cavity.

14. A method for measuring a physical property a fluid comprising the steps of:
    providing an optical cell having a fluid inlet and a fluid outlet;
    providing a light source;
    introducing a sample fluid into said optical cell;

passing light from said light source through said optical cell;

alternating a pressure of said fluid between a first positive pressure and a second positive pressure;

measuring an intensity of said light after passing through said optical cell at said first positive pressure and said second positive pressure; and determining a base intensity of said light after passing through said optical cell, where said base intensity corresponds to a zeroing intensity measured when said optical cell is filled with a purge gas.

15. The method of claim 14 further comprising determining an absorbance spectrum of said sample fluid, comparing said absorbance spectrum to a plurality of spectra located within a database, and determining at least one physical property of said sample fluid.

16. The method of claim 15, wherein said absorbance spectrum is determined by spatially dispersing said light after passing through said optical cell, forming a light spectrum, projecting said light spectrum onto a detector, and comparing said light spectrum with an actual spectrum of said light source.

17. The method of claim 16, wherein said light spectrum is digitized, forming a digitized light spectrum, and said digitized light spectrum is introduced into a data processing unit in which said actual spectrum of said light source is stored.

18. The method of claim 15, wherein said sample fluid is a combustible fluid and said physical property is a heating value of said combustible fluid.

19. The method of claim 15, wherein said sample fluid is a combustible fluid and said physical property is a composition of said combustible fluid.

* * * * *